(12) United States Patent
Chan et al.

(10) Patent No.: US 11,013,896 B2
(45) Date of Patent: May 25, 2021

(54) METHOD AND SYSTEM FOR EUSTACHIAN TUBE DILATION

(71) Applicant: Acclarent, Inc., Irvine, CA (US)

(72) Inventors: Randy S. Chan, San Jose, CA (US); Hung V. Ha, San Jose, CA (US); Andy Nguyen, San Jose, CA (US); Ketan P. Muni, San Jose, CA (US)

(73) Assignee: Acclarent, Inc., Irvine, CA (US)

(*) Notice: Subject to any disclaimer, the term of this patent is extended or adjusted under 35 U.S.C. 154(b) by 0 days.

(21) Appl. No.: 16/017,931

(22) Filed: Jun. 25, 2018

(65) Prior Publication Data

US 2018/0296811 A1 Oct. 18, 2018

Related U.S. Application Data

(63) Continuation of application No. 13/826,454, filed on Mar. 14, 2013, now abandoned.

(Continued)

(51) Int. Cl.
*A61M 3/02* (2006.01)
*A61B 1/06* (2006.01)
(Continued)

(52) U.S. Cl.
CPC .............. *A61M 29/02* (2013.01); *A61B 17/22* (2013.01); *A61B 17/24* (2013.01); *A61F 11/004* (2013.01);
(Continued)

(58) Field of Classification Search
CPC .......... A61M 25/0052; A61M 25/0053; A61M 25/0054; A61M 25/10; A61M 29/02;
(Continued)

(56) References Cited

U.S. PATENT DOCUMENTS 5,569,218 A 10/1996 Berg
6,716,813 B2 4/2004 Lim et al.
(Continued)

FOREIGN PATENT DOCUMENTS

CN 102159276 8/2011
JP 2012502749 2/2012

OTHER PUBLICATIONS

State Intellectual Property Office of People's Republic of China, Search Report, dated Jun. 17, 2016, 2 pgs.
(Continued)

*Primary Examiner* — Manuel A Mendez
*Assistant Examiner* — Justin L Zamory
(74) *Attorney, Agent, or Firm* — Frost Brown Todd LLC

(57) ABSTRACT

A device and method for dilating a Eustachian tube of a patient is disclosed. The device includes a guide catheter and a balloon dilation catheter. The balloon dilation catheter has an actuator that prevents injury to the middle ear. The balloon dilation catheter is slidably coupled with the guide catheter through the guide catheter lumen and is fully inserted into the guide catheter lumen when the distal side of the actuator is adjacent to the proximal end of the guide catheter. The method involves advancing the guide catheter and balloon dilation catheter through a nasal passage of the patient to dilate a portion of the Eustachian tube.

20 Claims, 9 Drawing Sheets

Related U.S. Application Data

(60) Provisional application No. 61/623,833, filed on Apr. 13, 2012.

(51) Int. Cl.

| | | |
|---|---|---|
| *A61M 29/02* | (2006.01) | |
| *A61M 29/00* | (2006.01) | |
| *A61B 17/22* | (2006.01) | |
| *A61B 17/24* | (2006.01) | |
| *A61F 11/00* | (2006.01) | |
| *A61M 25/06* | (2006.01) | |
| *A61M 25/10* | (2013.01) | |
| *A61M 25/01* | (2006.01) | |
| *A61B 17/00* | (2006.01) | |
| *A61M 25/00* | (2006.01) | |

(52) U.S. Cl.
CPC ........ *A61M 25/0662* (2013.01); *A61M 25/10* (2013.01); *A61M 29/00* (2013.01); *A61B 2017/00787* (2013.01); *A61B 2017/22051* (2013.01); *A61M 25/005* (2013.01); *A61M 25/0052* (2013.01); *A61M 25/0053* (2013.01); *A61M 25/01* (2013.01); *A61M 25/0105* (2013.01); *A61M 25/1036* (2013.01); *A61M 2025/0681* (2013.01); *A61M 2210/0675* (2013.01); *F04C 2270/0421* (2013.01)

(58) Field of Classification Search
CPC .. A61M 2210/0675; A61M 2025/0681; A61B 2017/22051; A61F 11/004
See application file for complete search history.

(56) References Cited

U.S. PATENT DOCUMENTS

| | | |
|---|---|---|
| 2006/0089618 A1 | 4/2006 | McFerran et al. |
| 2008/0172033 A1 | 7/2008 | Keith et al. |
| 2008/0195041 A1* | 8/2008 | Goldfarb ............... A61M 29/02 604/96.01 |
| 2010/0099946 A1 | 4/2010 | Jenkins et al. |
| 2010/0274188 A1* | 10/2010 | Chang .................... A61B 1/227 604/96.01 |
| 2011/0004057 A1 | 1/2011 | Goldfarb et al. |
| 2012/0071856 A1* | 3/2012 | Goldfarb ............... A61M 29/00 604/514 |
| 2012/0071857 A1 | 3/2012 | Goldfarb et al. |
| 2013/0274715 A1 | 10/2013 | Chan et al. |

OTHER PUBLICATIONS

The International Bureau of WIPO, IPER, dated Oct. 14, 2016, 10 pgs. Geneva CH.
ISR dated Jul. 19, 2013 International Appln. No. PCT/US2013/036430 filed Apr. 12, 2013.
First Chinese Office Action dated Jun. 27, 2016 for Application No. 201380019699.X, 11 pages.
Second Chinese Office Action dated Apr. 19, 2017 for Application No. 201380019699.X, 10 pages.
Third Chinese Office Action dated Dec. 25, 2017 for Application No. 201380019699.X, 10 pages.
Japanese Notification of Reasons for Refusal dated Feb. 8, 2017 for Application No. 2015-505954, 3 pages.
Japanese Notification of Reasons for Refusal dated Sep. 11, 2017 for Application No. 2015-505954, 4 pages.
Korean Office Action dated Nov. 19, 2019 for Application No. 10-2014-7031677, 5 pages.
Korean Office Action dated Mar. 24, 2020 for Application No. 10-2014-7031677, 1 page.

* cited by examiner

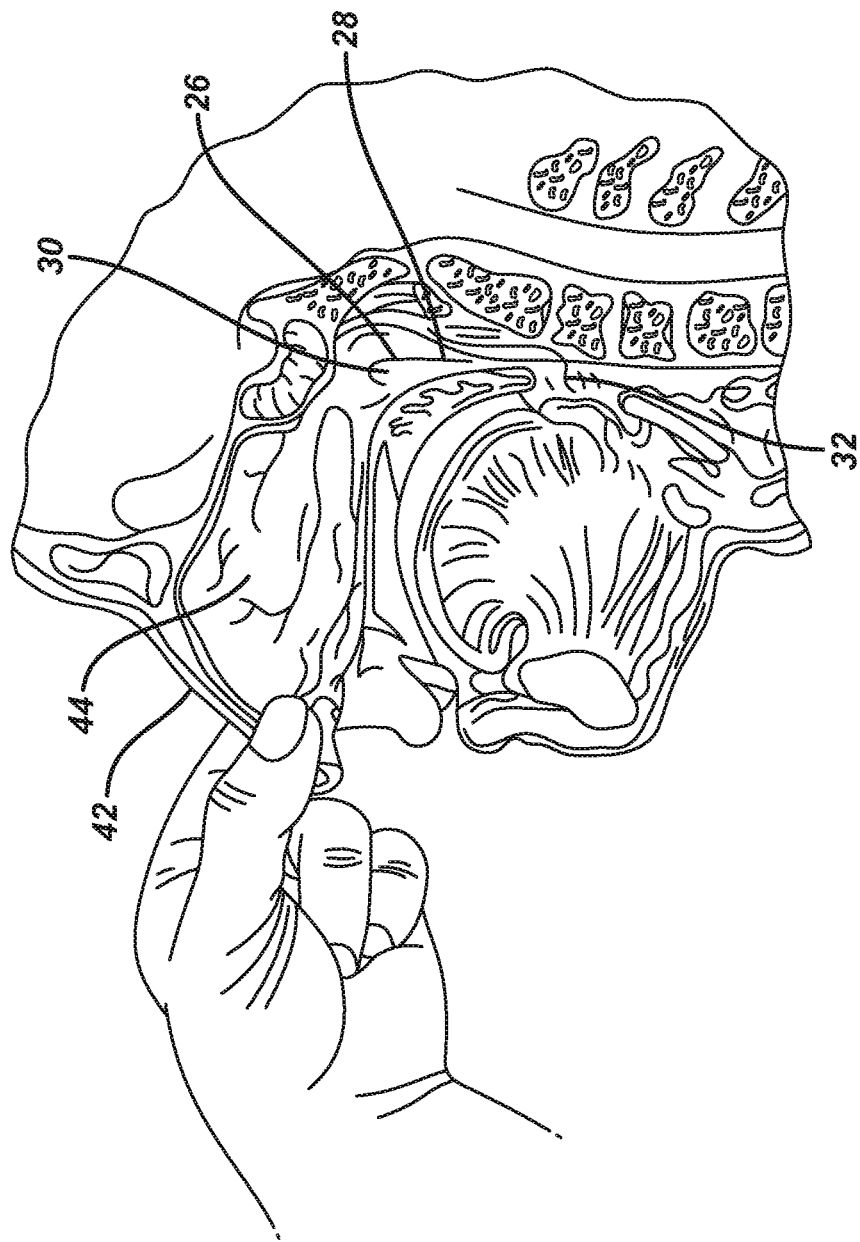
FIG. 6 *PRIOR ART*

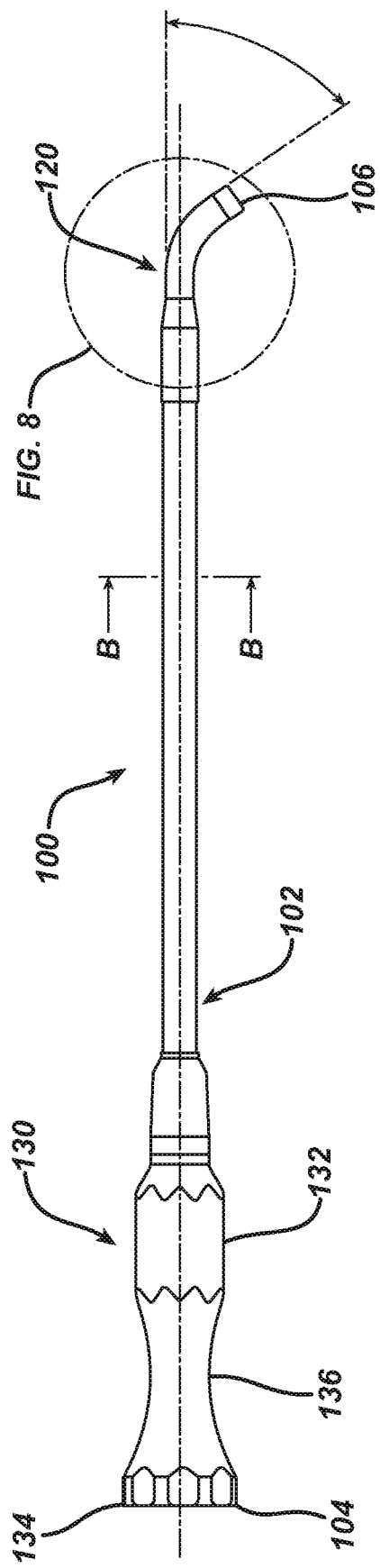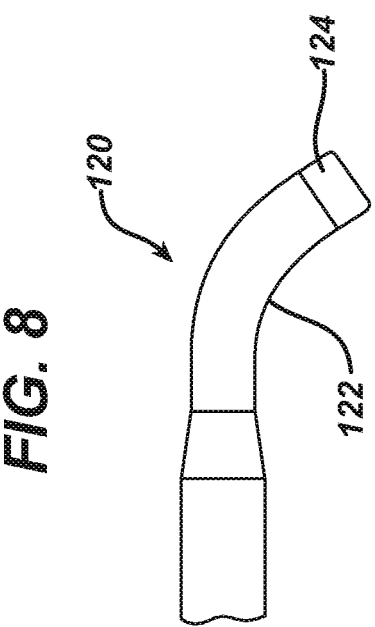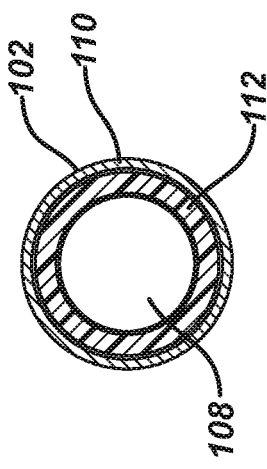

METHOD AND SYSTEM FOR EUSTACHIAN TUBE DILATION

RELATED APPLICATIONS

This application is a continuation of U.S. Non-provisional application Ser. No. 13/826,454 filed Mar. 14, 2013 entitled "Method and System for Eustachian Tube Dilation" which claims priority pursuant to 35 U.S.C. § 119 to U.S. Provisional Patent Application Ser. No. 61/623,833, entitled "Method and System for Eustachian Tube Dilation" filed on Apr. 13, 2012.

FIELD OF THE INVENTION

The present invention is related to methods and systems for accessing and treating target tissue regions within the middle ear and the Eustachian tube.

BACKGROUND OF THE INVENTION

Referring to FIGS. 1-2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a Eustachian tube 26 which serves as a pressure equalizing valve between the ear 10 and the sinuses. The Eustachian tube 26 terminates in a distal opening or ostium 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34-38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The Eustachian tube 26 is a narrow, two to two-and-a-half centimeter long channel, measured from the ostium 28 to the bony isthmus 29, connecting the middle ear 14 with the nasopharynx 30, the upper throat area just above the palate, in back of the nose. The Eustachian tube 26 functions as a pressure equalizing valve for the middle ear 14 which is normally filled with air. When functioning properly, the Eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the Eustachian tube 26 may result in hearing impairment or other ear symptoms.

Obstruction or blockage of the Eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition referred to as serous otitis media (fluid in the middle ear). This occurs frequently in children in connection with an upper respiratory infection and accounts for the hearing impairment associated with this condition.

A lining membrane (mucous membrane) of the middle ear 14 and Eustachian tube 26 is connected with, and is the same as, the membrane of the nose 42, sinuses 44 and throat 32. Infection of these areas results in mucous membrane swelling which in turn may result in obstruction of the Eustachian tube 26. This is referred to as serous otitis media, i.e. essentially a collection of fluid in the middle ear 14 that can be acute or chronic, usually the result of blockage of the distal opening 28 of the Eustachian tube 26 which allows fluid to accumulate in the middle ear 14. In the presence of bacteria, this fluid may become infected, leading to an acute suppurative otitis media (infected or abscessed middle ear). When infection does not develop, the fluid remains until the Eustachian tube 26 again begins to function normally, at which time the fluid is absorbed or drains down the tube into the throat 32 through the Eustachian tube opening 28.

Chronic serous otitis media may result from longstanding Eustachian tube blockage, or from thickening of the fluid so that it cannot be absorbed or drained down the Eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the Eustachian tube 26 contains a build-up of fluid, a number of things will occur. First, the body absorbs the air from the middle ear 14, causing a vacuum to form which tends to pull the lining membrane and ear drum 22 inward, causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected, which is painful and makes the patient feel ill and which may cause the patient not to be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14; i.e. the most immediate relief will be felt by the patient if the fluid can be removed from the Eustachian tube 26.

Antibiotic treatment of middle ear infections typically results in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the Eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to ensure ventilation of the middle ear 14. The ventilation tube 44 temporarily takes the place of the Eustachian tube 26 in equalizing the pressure in the middle ear 14. The ventilation tube 44 usually remains in place for three to nine months during which time the Eustachian tube 26 blockage subsides. When the tube 44 dislodges, the eardrum 22 heals; the Eustachian tube 26 then resumes its normal pressure equalizing function.

Another method of relieving the pressure in the middle ear 14 is shown in FIG. 4 in which a hypodermic needle 46 is driven through the eardrum 22 through which any accumulated fluid can be withdrawn from typically only the upper portion of the Eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the Eustachian tube 26 since often the lower end 28 thereof is blocked and dammed with fluid.

In connection with the above surgical treatments of FIGS. 3 and 4, Eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the Eustachian tube 26 in the nasopharynx region 30 of the throat 32. Air is blown through the tip 48 via the syringe 46 into the obstructed Eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This procedure forces air into the Eustachian tube 26 and the middle ear 14. This technique is good for opening the Eustachian tube 26 but it does not clear accumulated fluid away.

Another method for clearing the middle ear 14 (at least temporarily) is referred to as the "valsalva" maneuver, accomplished by forcibly blowing air into the middle ear 14 while holding the nose, often called popping the ear. This method is also good for opening the Eustachian tube 26 but it does not clear the accumulated fluid away either.

Typical disorders associated with the middle ear and the Eustachian tube include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the ear drum. However, ear surgery can also require the removal of the tympanic membrane for the visualization of the middle ear space. Often surgeons will try to preserve the integrity of the membrane by making incisions in the skin of the ear canal and removing the tympanic membrane as a complete unit. Alternatively, middle ear access is achieved via the mastoids. This method approaches the middle ear space from behind the ear and drills through the mastoid air cells to the middle ear. Whether the bony partition between the external ear canal and the mastoid is removed or not depends on the extent of the disease. Canal-wall-down refers to the removal of this bony partition. Canal-wall-up refers to keeping this bony partition intact. The term modified radical mastoidectomy refers to an operation where this bony partition is removed and the eardrum and ossicles are reconstructed. A radical mastoidectomy is an operation where this bony partition is removed and the ear drum, malleus and incus bones are permanently removed so that the inner lining of the large cholesteotoma sac can be safely cleaned. This operation is done when an extensive cholesteotoma is encountered or one that is adherent to the inner ear or facial nerve.

Afflictions of the middle ear and Eustachian tube are very prevalent and a serious medical problem, afflicting millions of people and causing pain, discomfort and even hearing loss or permanent ear damage. Although a number of treatments have been developed, as described above each of them have shortcomings. Therefore, a need exists for improved methods and systems for accessing, diagnosing and treating target tissue regions within the middle ear and the Eustachian tube. Ideally, such methods and systems would be minimally invasive and pose very little risk of damage to healthy ear tissue.

US Patent Publication No. 2010/0274188, now abandoned, which is incorporated by reference herein in its entirety is directed toward methods and systems for accessing, diagnosing and treating target tissue regions within the middle ear and the Eustachian tube. One particular method described in the publication is for dilating a Eustachian tube of a patient. A guide catheter may be advanced through a nasal passage of the patient to position a distal end of the guide catheter at or near an opening of the Eustachian tube of the patient. A distal portion of the guide catheter may include a bend having an angle between 30 and 90 degrees. The distal portion may be more flexible than a proximal portion of the guide catheter. A guidewire may be advanced through the guide catheter such that a distal end of the guidewire enters the Eustachian tube. A dilation catheter may be advanced over the guidewire to position a dilator of the dilation catheter within the Eustachian tube. The dilator may be expanded to dilate the Eustachian tube. The dilation catheter and guidewire may be removed from the patient.

Improvement in the devices described above would provide a system for dilation of the Eustachian tube that would be ergonomic and easy to use and would safely and effectively access the Eustachian tube without the need for a guidewire.

SUMMARY OF THE INVENTION

The present invention provides devices and methods for accessing and treating the Eustachian tube of a patient.

In one aspect, a medical device is provided for dilating a Eustachian tube of a patient. The device includes a guide catheter and a balloon dilation catheter. The guide catheter has an elongate shaft that has a proximal end and a distal end and a lumen therebetween. The guide catheter further has a proximal hub attached to the proximal end of the elongate shaft. The balloon dilation catheter has an elongate shaft. The elongate shaft has a proximal end and a distal end. The balloon dilation catheter has an actuator for one-handed advancement of the catheter coupled to the elongate shaft between the elongate shaft proximal end and the elongate shaft distal end. The actuator separates the elongate shaft into a proximal portion and a distal portion. The actuator has a proximal side and a distal side. The balloon dilation catheter is slidably coupled with the guide catheter through the guide catheter lumen and is fully inserted into the guide catheter lumen when the distal side of the actuator is adjacent to the proximal end of the guide catheter.

In one embodiment, the balloon dilation catheter comprises an inflatable balloon and a proximal connector. The proximal connector has an inflation port in fluid communication with an inflation lumen of the balloon catheter.

In another embodiment, the proximal connector further includes an injection port.

In yet another embodiment the guide catheter elongate shaft has a bend with an angle of between about 45 degrees and about 65 degrees. In one embodiment, the guide catheter elongate shaft has a bend with an angle of about 55.

In still another embodiment, the distal end of the balloon dilatation catheter shaft has a bulbous tip.

In a further embodiment, the balloon dilation catheter has a flexible proximal portion and a rigid distal portion. In one embodiment, the rigid distal portion comprises a hypotube.

In another aspect, the invention includes a method for dilating a Eustachian tube of a patient. The method includes advancing a guide catheter through a nasal passage of the patient to position the guide catheter adjacent the Eustachian tube. The guide catheter has an elongate shaft, the elongate shaft has a proximal end and a distal end and a lumen therebetween. The guide catheter has a proximal hub attached to the proximal end of the elongate shaft. The method further includes advancing a balloon dilation catheter through the lumen of the guide catheter until the distal side of the actuator is adjacent to the proximal end of the guide catheter. The balloon dilation catheter has an elongate shaft and a balloon attached to the elongate shaft. The elongate shaft has a proximal end and a distal end. The balloon dilation catheter has an actuator coupled to the elongate shaft between the elongate shaft proximal end and the elongate shaft distal end. The actuator separates the elongate shaft into a proximal portion and a distal portion. The actuator has a proximal side and a distal side. The method further includes expanding the balloon to dilate a portion of the Eustachian tube, collapsing the balloon; and removing the guide catheter and balloon dilation catheter from the patient. The dilated portion of the Eustachian tube remains at least partially dilated after removal of the device.

In one embodiment of the method, the guide catheter includes a distal portion with bend of between about 45 degrees and about 65 degrees.

In a further embodiment, the opening of the Eustachian tube includes a pharyngeal ostium of the Eustachian tube, and the balloon dilation catheter is advanced to position the balloon in the pharyngeal ostium.

In yet another embodiment, the method of claim includes advancing an endoscope through the nasal passage and viewing at least one of the advancing, expanding, collapsing or removing steps using the endoscope.

In a further embodiment, the viewing includes viewing a marker on the balloon dilation catheter, and further includes approximating a location of the balloon dilation catheter relative to the opening of the Eustachian tube based on a distance of the marker from a proximal end of the dilator.

In still another embodiment, the method includes applying at least one substance to the Eustachian tube using the balloon dilation catheter.

In a further aspect, the method for dilating a Eustachian tube of a patient having a nostril includes advancing a balloon dilation catheter through the nostril of the patient until the distal side of the actuator is adjacent to the nostril of the patient. The balloon dilation catheter has an elongate shaft and a balloon attached to the elongate shaft. The elongate shaft has a proximal end and a distal end. The balloon dilation catheter has an actuator coupled to the elongate shaft between the elongate shaft proximal end and the elongate shaft distal end. The actuator separates the elongate shaft into a proximal portion and a distal portion, and the actuator has a proximal side and a distal side. The method further includes expanding the balloon to dilate a portion of the Eustachian tube, collapsing the balloon and removing the balloon dilation catheter from the nostril of the patient. The dilated portion of the Eustachian tube remains at least partially dilated after removal of the device.

In one embodiment the balloon dilation catheter is advanced to position the balloon in the pharyngeal ostium.

In another embodiment, the method further includes advancing an endoscope through the nasal passage, and viewing at least one of the advancing, expanding, collapsing or removing steps using the endoscope.

In yet another embodiment the method includes viewing a marker on the balloon dilation catheter and approximating a location of the balloon dilation catheter relative to the opening of the Eustachian tube based on a distance of the marker from a proximal end of the dilator.

In still another embodiment the method includes applying at least one substance to the Eustachian tube using the balloon dilation catheter.

In another aspect, the invention is directed to a device for accessing the Eustachian tube through the nose of a human patient. The device includes a guide catheter having an elongate shaft with a bend angle of between about 45 and 65 degrees and with a proximal end and a distal end. A proximal hub is attached to the proximal end of the shaft. The proximal hub is positioned on the elongate shaft such that when the guide catheter is positioned fully within the nose of a human patient the proximal hub abuts the nose. In one embodiment the lumen of the elongate shaft is adapted for delivering a substance therethrough.

In yet another aspect, the invention is directed to a balloon dilation catheter for accessing and treating the Eustachian tube through the nose of a human patient. The balloon dilation catheter includes an elongate shaft, an actuator, an inflatable balloon and a proximal connector. The elongate shaft has a proximal end and a distal end and an inflation lumen therebetween. The actuator is useful for one-handed advancement of the catheter and is coupled to the elongate shaft between the elongate shaft proximal end and the distal end, and is positioned on the elongate shaft such that when the balloon dilation catheter is positioned fully within the nose of the human patient, the actuator abuts the nose of the human patient. The proximal connector comprises an inflation port in fluid communication with lumen of the elongate shaft and an injection port. In one embodiment, the inflation port comprises a first type of connector and the injection port comprises a second type of connector different from the first type of connector.

For a further understanding of the nature and advantages of the invention, reference should be made to the following description taken in conjunction with the accompanying figures. Each of the figures is provided for the purpose of illustration and description only and is not intended to limit the scope of the embodiments of the present invention.

BRIEF DESCRIPTION OF THE DRAWINGS

FIGS. 5-6 show a cross-section of a human head in the orientation shown in FIG. 2 showing a prior art politzeration method for relieving fluid in the middle ear in which a syringe is shown having a flexible tip extending into the nose and/or throat area so that the tip abuts the distal opening of the Eustachian tube while the nose is plugged.

FIG. 7A is a simplified side view of a guide catheter useful for positioning the catheter of FIG. 9A.

FIG. 7B is a cross-sectional view of the guide catheter shown in FIG. 7A through line B-B of FIG. 7A.

FIG. 8 is an enlarged view of the distal end of the guide catheter shown in FIG. 7A.

DETAILED DESCRIPTION OF THE INVENTION

Figure 1:
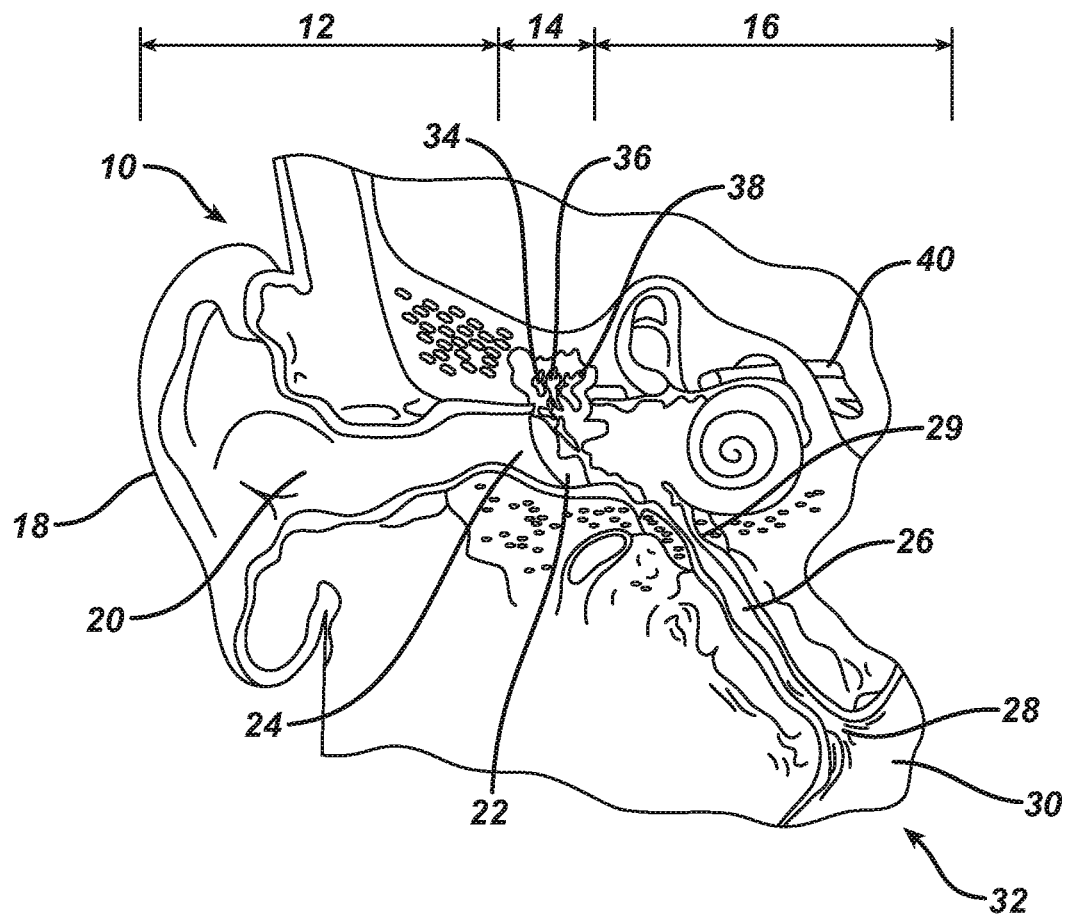
FIG. 1 is a cross-section of a human ear showing the inner, middle and outer ear portions and the Eustachian tube connecting the middle ear with the nasopharynx region of the throat via a distal opening thereof.
Figure 2:
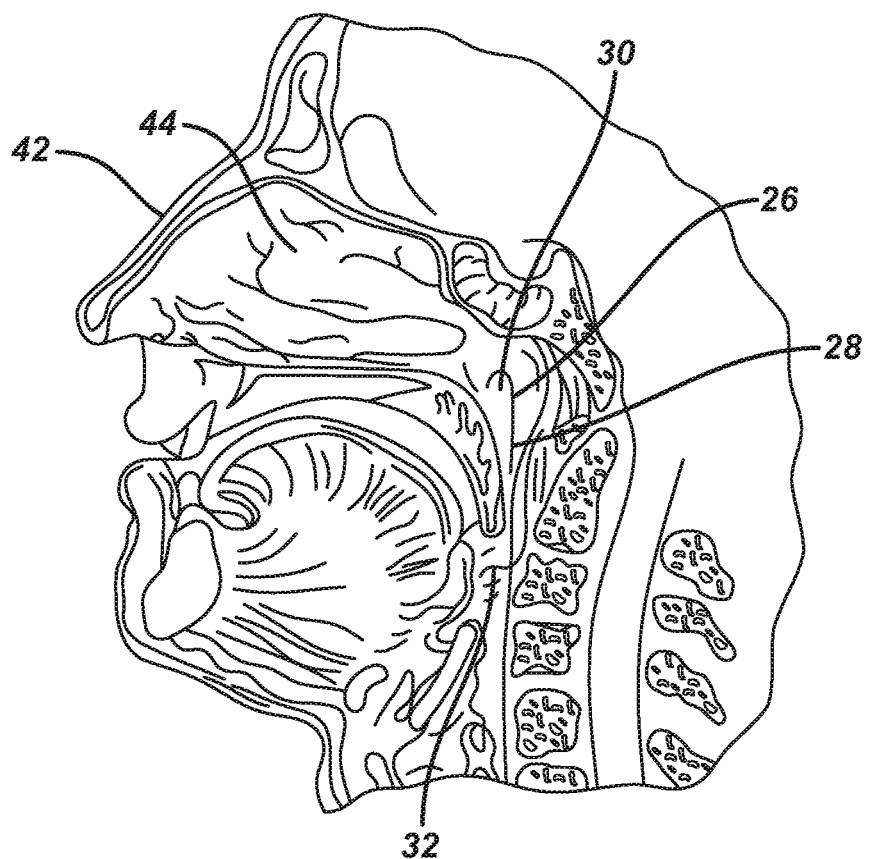
FIG. 2 is a cross-section of a human head showing the nasopharynx region of the throat illustrated in FIG. 1 containing the distal opening of the Eustachian tube illustrated in FIG. 1.
Figure 3:
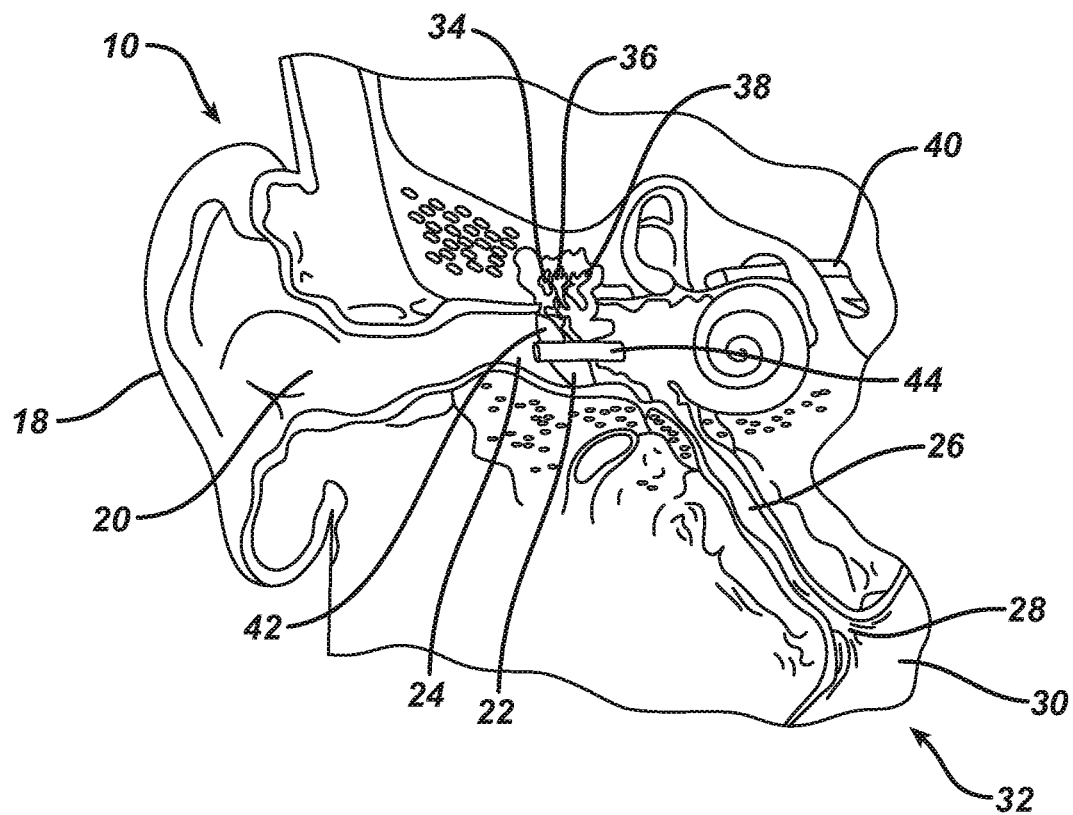
FIG. 3 is a cross-section of a human ear in the orientation shown in FIG. 1 showing a prior art surgical method for relieving fluid in the middle ear in which a ventilation tube is placed within an incision in the eardrum.
Figure 4:
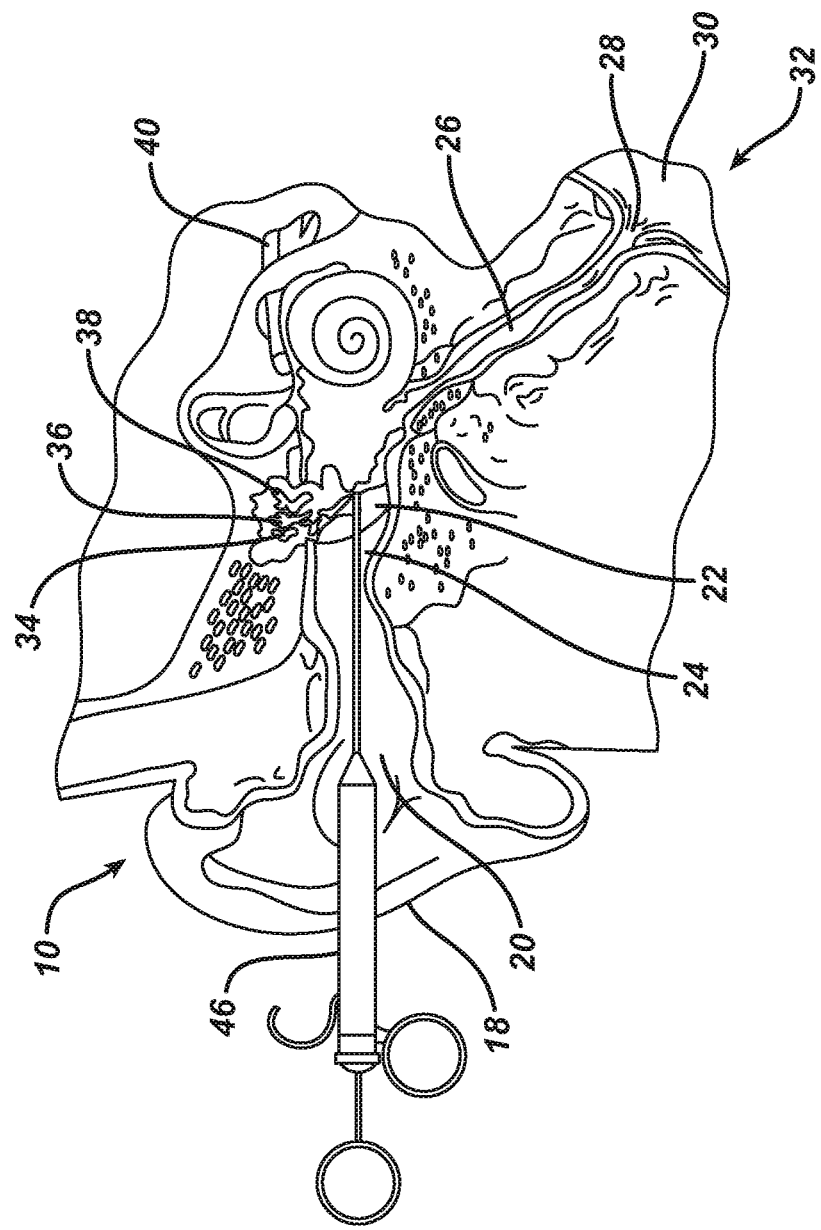
FIG. 4 is a cross-section of a human ear in the orientation shown in FIG. 1 showing a prior art surgical method for relieving fluid in the middle ear in which a syringe is shown having a needle perforating the eardrum.
Figure 5:
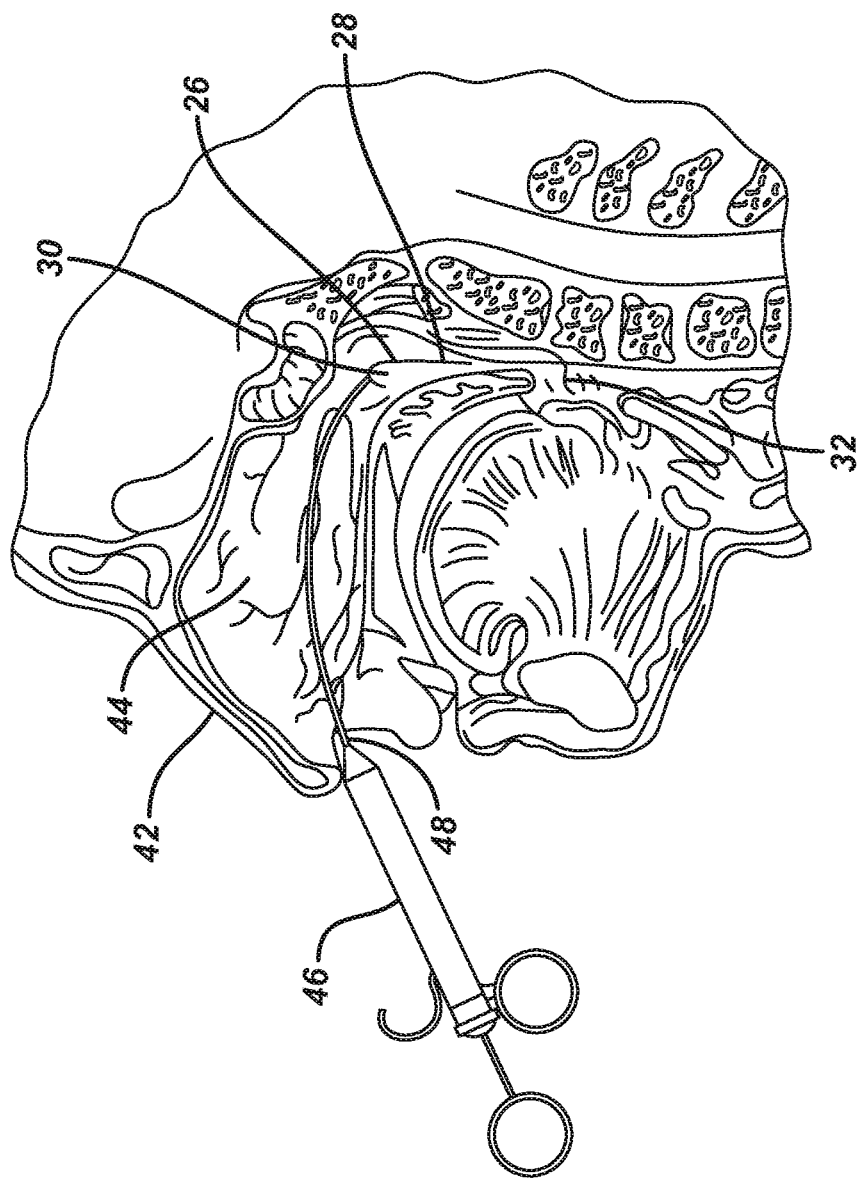

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

The embodiments of the present invention are directed toward methods and systems for easily accessing and treating target tissue regions within the middle ear and the Eustachian tube using a system that can be operated with one hand and without damaging structures in the middle ear.

In various alternative embodiments the invention includes a guide catheter 100 and a balloon dilation catheter 200 operable in combination with a single hand.

One embodiment of the guide catheter 100 of the invention is shown in FIG. 7A. As shown, the guide catheter 100 includes an elongate tubular shaft 102 that has a proximal end 104, a distal end 106 and a lumen 108 therebetween. The guide catheter 100 may have any suitable length, diameter, angle of bend, and location of the bend along the length of the catheter 100, to facilitate accessing a Eustachian tube opening. In some embodiments, for example, the guide catheter 100 may have a length between about 8 cm and about 20 cm, and more preferably between about 10 cm and about 15 cm and often about 11 cm.

FIG. 7B is a cross-sectional view of the guide catheter elongate tubular shaft 102. As can be seen, the shaft has an outer shaft tube 110, an inner shaft tube 112 and a lumen 108. The outer shaft tube 110 may be constructed of a stiff material such as stainless steel and the inner shaft tube 112 may be constructed of a more flexible material such as a polymeric material including but not limited to nylon and further including a PTFE liner. The lumen 108 has a diameter of between about 2 mm and 3 mm preferably between about 2.5 mm and 2.6 mm such that the balloon dilation catheter 200 can be easily inserted into the lumen 108 for dilation of the Eustachian tube 26. The combination guide catheter 100 and balloon catheter 200 may a compact system that is designed for a one-handed procedure. By compact is intended that the length of the guide catheter shaft that is distal of the bend in the guide catheter is between about 0.5 and 2.0 cm, often between about 1 and 2 cm and often about 1 cm. The compactness helps reduce interference with other instruments, such as an endoscope that may be used to help in visualizing the positioning of the system.

The distal portion 120 of guide catheter 100 is shown in an enlarged view in FIG. 8. The distal portion 120 of the guide catheter 100 may have a bend 122 with an angle between about 45 degrees and about 65 degrees, and more preferably between about 50 degrees and about 60 degrees and often about 55 degrees to facilitate access into the Eustachian tube 26. The distal portion 120 of the guide catheter 100 is made of a transparent material such as a polymer including but not limited to nylon and PTFE such that the balloon dilation catheter is visible within the distal portion 120 and is more flexible than the elongate shaft 102. The distal tip 124 of the distal portion 120 of the guide catheter 100 is made of pebax such that it provides for atraumatic access to the Eustachian tube, and may contain 20% barium sulfate or other similar radiopaque materials for visualizable access.

Referring again to FIG. 7A, the proximal portion 130 of guide catheter 100 includes a proximal hub 132 to aid in insertion of the balloon catheter into the Eustachian Tube 26. The hub 132 has a larger diameter proximal end 134 and a smaller diameter middle section 136 to facilitate stabilization of the guide catheter 100 in the nose, rotation of the guide catheter 100 and insertion of the balloon catheter 200 as will be described in further detail below. The hub 132 is ergonomically designed for insertion, location and rotation with slight manipulations with one hand.

Figure 11:
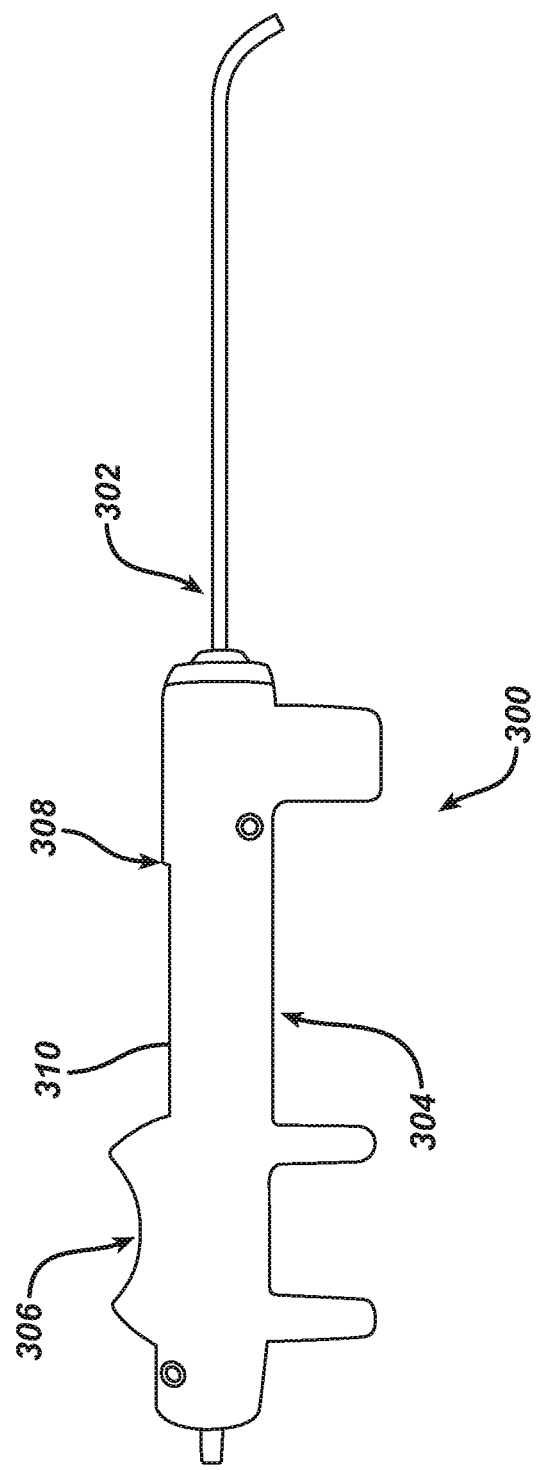
FIG. 11 is a simplified view of a guide catheter according to a further embodiment of the invention.

A further embodiment of the guide catheter 300 according to the invention is shown in FIG. 11. In this embodiment, the proximal hub is a handle. The guide catheter comprises an elongate shaft 302 and a handle 304 to aid in insertion of the balloon catheter (not shown) into the Eustachian Tube 26 in a manner similar to that described below with regard to the guide catheter shown in FIG. 7A. In the embodiment shown in FIG. 11, the actuator 302 comprises a slider that is attached to the balloon catheter that is contained within the handles 304 and is slidably contained within the elongate shaft 302 of the guide catheter. In use, the guide catheter is inserted into the sinus of the patient and the balloon catheter is advanced into the Eustachian tube via thumb or single finger advancement of the actuator 302 along the handle 304. The advancement of the balloon catheter is continued until a visual marker indicates that advancement is complete, or until the enlarged tip of the balloon catheter abuts the isthmus of the Eustachian tube or the actuator abuts the distal end 308 of the opening 310 in the handle 304 and is therefore fully deployed.

Figure 9A:
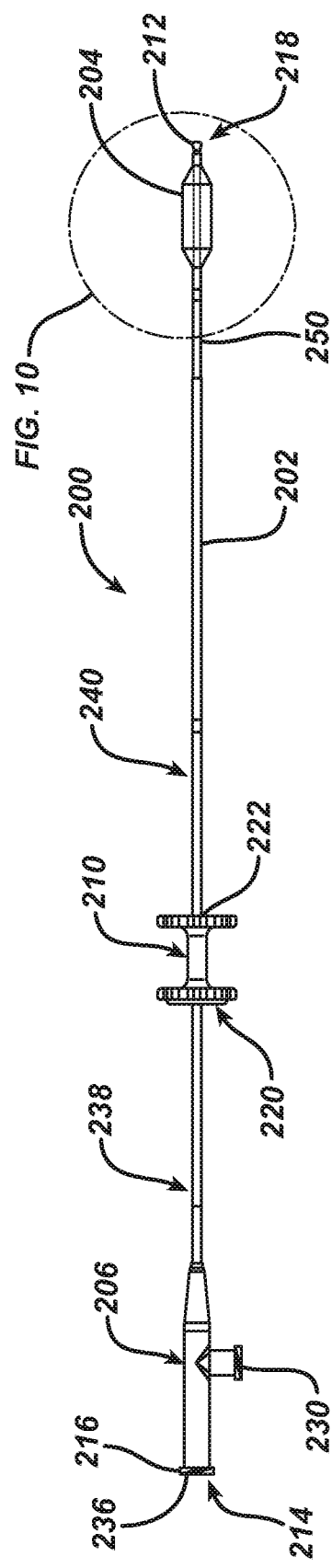
FIG. 9A is a simplified side view of a balloon dilation catheter according to an embodiment of the present invention.
Figure 10:
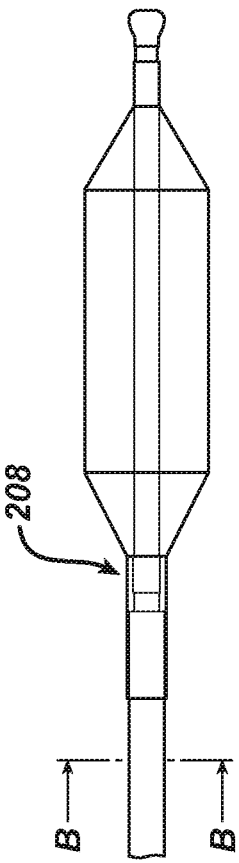
FIG. 10 is an enlarged view of the distal end of the balloon dilation catheter shown in FIG. 9A.

The balloon dilation catheter of the invention is shown in FIG. 9A. The balloon dilation catheter 200 generally includes an elongate shaft 202 having a proximal end 214 and a distal end 218. The balloon dilation catheter 200 further includes a balloon 204 on the distal end 218 of the elongate shaft 202. The balloon 204 may be a polymer balloon (compliant, semi-compliant or non-compliant). In one embodiment, the balloon may be a suitable non-compliant material such as but not limited to polyethylene terephalate (PET), PEBAX, nylon or the like. The balloon catheter may include any size of balloon including but not limited to balloons of 2 mm to 8 mm in diameter or of between about 5 mm and 6 mm (when inflated) and 12 mm to 24 mm in working length (for example 2 mm×12 mm, 3.5 mm×12 mm, 5 mm×16 mm, 5 mm×24 mm, 6 mm×16 mm, 6 mm×20 mm, 6 mm×24 mm, 7 mm×16 mm and 7 mm×24 mm). The balloon dilation catheter 200 generally includes a proximally located connection 230 for inflating/activating the balloon 204.

The balloon 204 may be expanded to dilate the Eustachian tube ET after it is placed in a desirable location therein. For example, the opening area of the Eustachian tube ET includes a pharyngeal ostium, and the dilation catheter 200 may be advanced to position the balloon in the pharyngeal ostium. An endoscope may be used to assist in positioning the dilation catheter 200. The endoscope may be advanced through the nasal passage to view the dilation catheter 200. A marker 208 on a shaft of the dilation catheter 200 can be viewed from the endoscope to approximate a location of the balloon 204 relative to the opening of the Eustachian tube ET based on a distance of the marker 208 from a proximal end of the balloon 204. Accordingly, the dilation catheter 200 can be moved to place the marker in a desirable location before expansion of the balloon 204 in the Eustachian tube ET.

The balloon dilation catheter further includes an actuator 210. The actuator 210 has a proximal side 220 and a distal side 222. In the embodiment shown in FIG. 9A, the actuator 210 is secured by an adhesive to the elongate shaft 202. The portion 240 of the elongate shaft 202 that is distal of the actuator 210 is sufficiently stiff to be guided through the nasal cavity and into the Eustachian Tube and is constructed of stainless steel and preferably includes a stainless steel hypotube. The portion 238 of the elongate shaft 202 that is proximal of the actuator 210 and that portion 250 that is distal of portion 240 is more flexible than the portion 240 and is constructed of a polymeric material including but not limited to pebax. In this way, the proximal portion 238 of the elongate shaft 202 will not interfere with the endoscope described above as it is advanced through the nasal passage such that the dilation catheter 200 can be easily viewed. The actuator 210 allows for easy, ergonomic one-handed advancement of the dilation 200 catheter through the guide catheter 100 and into the Eustachian Tube ET. The actuator 210 may be used to advance or retract in alternative ways including but not limited to use of the thumb, the index finger, or a combination of fingers (i.e. the index and middle fingers) or the thumb and the index or middle finger.

Figure 9B:
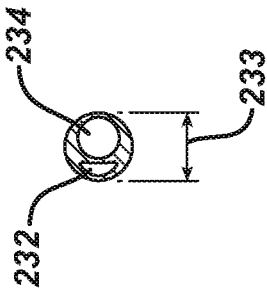
FIG. 9B is a cross-sectional view of the balloon dilation catheter shown in FIGS. 9A and 10 through line B-B of FIG. 10.

The distal end 218 of the balloon catheter 200 further includes a tip 212 and a flexible shaft portion 250 that is constructed of a polymeric material including but not limited to pebax that extends from the distal end of the elongate shaft 202 to the proximal end of the balloon 204. In the embodiment shown in FIG. 9A, the tip 212 is a bulbous polymeric blueberry shaped tip that is atraumatic and is about 1.5 mm to 2 mm in length with an outer diameter of between about 2 mm and 3 mm. The smoothness and roundness of tip 212 facilitates advancement of the balloon catheter 200 by helping it glide smoothly through the Eustachian Tube ET. The tip further acts as a safety stop. The isthmus 29 of the Eustachian Tube, shown in FIG. 1 is approximately 1 mm in diameter. The tip diameter is larger than the outer diameter 233 of the elongate shaft 202 shown in cross-section in FIG. 9B such that the tip 212 size will prevent the balloon catheter 200 from passing through the isthmus 29 into the middle ear 14.

The balloon 204 may be held in location while in an expanded state for an extended period of time (e.g. several seconds or minutes). The balloon catheter 200 may also deliver a substance to the Eustachian tube ET, such as one or more of the therapeutic or diagnostic agents described herein. The balloon 204 may also carry an expandable stent for delivery into the Eustachian tube upon expansion of the balloon 204. The balloon dilation catheter 200 and the guide catheter may be removed from the patient after the balloon 204 has been deflated/unexpanded. The Eustachian tube will resume functioning, normally opening and closing to equalize atmospheric pressure in the middle ear and protect the middle ear from unwanted pressure fluctuations and loud sounds.

In use, the guide catheter 100 may be advanced into a nostril and through a nasal cavity to position a distal end of the catheter 100 at, in or near an opening into the Eustachian tube. In one embodiment, the guide catheter 100 may be passed through a nostril to the Eustachian tube on the ipsilateral (same side) of the head. In an alternative embodiment, the guide catheter 100 may be passed through a nostril to the Eustachian tube on the contralateral (opposite side) of the head. A guiding element such as a guidewire or illuminating fiber may be used to aid in accessing the Eustachian Tube.

After the guide catheter 100 is in a desired position, a balloon catheter 200 is advanced through the guide catheter 100 to position a balloon 204 of the balloon catheter 200 within the Eustachian tube ET. The physician/user may place the index and middle fingers on either side of the smaller diameter middle section 136 of the proximal hub 132 of the guide catheter 100. The physician/user will then place the thumb on the proximal side 220 of the actuator 210 or within both sides of the actuator 210 and will use the thumb to slide the balloon dilation catheter 200 through the guide catheter 100 to position the balloon within the Eustachian tube ET. Alternatively, the user may grasp the proximal hub 132 of the guide catheter 100 and use the index finger placed on the proximal side 220 of the actuator 210 or in between the distal side 222 and the proximal side 220 of the actuator 210 to advance the balloon catheter 200. The larger diameter tip 212 prevents the balloon catheter 200 from advancing too far into the middle ear. Further, the distal side 222 of the actuator 210 will bottom out against the proximal end 104 of the guide catheter 100, such that the balloon catheter cannot advance any further. The actuator 210 prevents the catheter from reaching too far into the middle ear, which can cause damage to structures in the middle ear. Further the actuator 210 can be positioned at the appropriate distance along the elongate shaft 202 such that access to the Eustachian tube may be from the contralateral or the ipsilateral side.

In an alternative embodiment, a balloon catheter 200 is advanced into a nostril of a patient without the use of a guide catheter. The balloon 204 of the balloon catheter 200 is placed within the Eustachian tube ET. The physician/user will advance the balloon catheter 200 until the proximal side 220 of the actuator 210 is adjacent the patient's nostril. The distal side 222 of the actuator 210 will bottom out against the patient's nostril, such that the balloon catheter cannot advance any further. The actuator 210 prevents the catheter from reaching too far into the middle ear, which can cause damage to structures in the middle ear. Further the actuator 210 can be positioned at the appropriate distance along the elongate shaft 202 such that access to the Eustachian tube may be from the contralateral or the ipsilateral side.

Following placement of the balloon catheter into the desired position any number of procedures may be carried out. The elongate shaft 202 contains adjacent dual lumen tubing (see FIG. 9B). By adjacent dual lumen tubing is intended that the lumens are next to each other but are spaced apart, one from the other. The inflation lumen 232 is used for inflation of the balloon with water, contrast medium or saline through inflation port 230 to a pressure of between about 3 and 15 atmospheres, or of between about 6 and 12 atmospheres. The injection lumen 234 permits the optional injection of water, medicament, or even the introduction of a guidewire through the injection port 236 at the proximal end 216 of the proximal connector 206. In order to ensure that the inflation port 230 is used for balloon inflation only, the inflation port 230 and the injection port 236 may optionally be different type connectors. For example, the inflation port may be a female connector whereas the injection port is a male connector or vice versa. Alternatively, the injection port may be a right-handed thread connected and the inflation port may have a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, piperacillini-tazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112" manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular embodiment, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one embodiment, a local anesthetic, such as Lidocaine is injected through the injection lumen 234 prior to dilation of the Eustachian Tube. The injection lumen 234 can be used for venting during dilation so that pressure in the middle ear does not increase or decrease.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A method for dilating a Eustachian tube of a patient, the method comprising:
   (a) advancing a guide catheter including a first elongate shaft through a nasal passage of the patient to position the guide catheter adjacent the Eustachian tube, the first elongate shaft having a proximal end, a distal end, and a lumen therebetween, the guide catheter including a proximal hub attached to the proximal end of the first elongate shaft;
   (b) inserting a balloon dilation catheter that includes a second elongate shaft and a balloon attached to the second elongate shaft into the nasal passage, the second elongate shaft having a proximal end and a distal end, the balloon dilation catheter including an actuator that is coupled to the second elongate shaft between the proximal and distal ends of the second elongate shaft, the actuator separating the second elongate shaft into a flexible proximal portion and a distal portion, the distal portion having a rigid middle portion and a flexible distal portion, the actuator including a proximal flange extending orthogonally from an axis defined by the second elongate shaft, a distal flange extending orthogonally from the axis of the second elongate shaft, and a space disposed between the proximal and distal flanges;
   (c) advancing the balloon dilation catheter through the lumen of the guide catheter by moving the actuator using a user's thumb or index finger either on a proximal side of the proximal flange or in the space between the proximal and distal flanges until the distal flange of the actuator is adjacent to the proximal end of the guide catheter;
   (d) expanding the balloon to dilate a portion of the Eustachian tube;
   (e) collapsing the balloon; and
   (f) removing the guide catheter and the balloon dilation catheter from the patient, wherein the dilated portion of the Eustachian tube remains at least partially dilated after removing the guide catheter and the balloon dilation catheter.

2. The method of claim 1, wherein the guide catheter includes a distal portion with a bend of between about 45 degrees and about 65 degrees.

3. The method of claim 1, wherein the Eustachian tube comprises a pharyngeal ostium, and wherein the balloon dilation catheter is advanced to position the balloon in the pharyngeal ostium.

4. The method of claim 1, further comprising:
   (a) advancing an endoscope through the nasal passage; and
   (b) viewing at least one of the advancing, expanding, collapsing or removing steps using the endoscope.

5. The method of claim 4, wherein viewing includes viewing a marker on the balloon dilation catheter, and wherein the method further comprises approximating a location of the balloon dilation catheter relative to an opening of the Eustachian tube based on a distance of the marker from a proximal end of the balloon.

6. The method of claim 1, further comprising applying at least one substance to the Eustachian tube using the balloon dilation catheter.

7. The method of claim 1, wherein the actuator allows for ergonomic one-handed advancement of the balloon dilation catheter through the guide catheter and into the Eustachian tube.

8. The method of claim 1, wherein advancing the balloon dilation catheter through the lumen of the guide catheter until the distal flange of the actuator is adjacent to the proximal end of the guide catheter prevents the balloon dilation catheter from reaching too far into a middle ear of the patient.

9. The method of claim 1, wherein advancing the balloon dilation catheter further comprises advancing the balloon dilation catheter through the lumen of the guide catheter by moving the actuator using the user's thumb or index finger disposed in the space, until the distal flange of the actuator is adjacent to the proximal end of the guide catheter.

10. A method for dilating a Eustachian tube of a patient having a nostril, the method comprising:
    (a) inserting a balloon dilation catheter that includes an elongate shaft and a balloon attached to the elongate shaft into the nostril of the patient, the elongate shaft having a proximal end and a distal end, the balloon dilation catheter including an actuator coupled to the elongate shaft between the proximal and distal ends of the elongate shaft, wherein the actuator separates the elongate shaft into a flexible proximal portion and a distal portion, the distal portion having a rigid middle portion and a flexible distal portion, the actuator including a proximal flange extending orthogonally from an axis defined by the elongate shaft, a distal flange extending orthogonally from the axis of the elongate shaft, and a space disposed between the proximal and distal flanges;
    (b) advancing the balloon dilation catheter by moving the actuator using a user's thumb or index finger either on a proximal side of the proximal flange or in the space between the proximal and distal flanges, until the distal flange of the actuator is adjacent to the nostril of the patient;
    (c) expanding the balloon to dilate a portion of the Eustachian tube;
    (d) collapsing the balloon; and
    (e) removing the balloon dilation catheter from the nostril of the patient, wherein the dilated portion of the Eustachian tube remains at least partially dilated after removing the balloon dilation catheter.

11. The method of claim 10, wherein the Eustachian tube comprises a pharyngeal ostium, and wherein advancing the balloon dilation catheter further comprises advancing the balloon dilation catheter to position the balloon in the pharyngeal ostium.

12. The method of claim 10, further comprising:
    (a) advancing an endoscope into the nostril; and
    (b) viewing at least one of the advancing, expanding, collapsing or removing steps using the endoscope.

13. The method of claim 12, wherein viewing includes viewing a marker on the balloon dilation catheter, and wherein the method further comprises approximating a location of the balloon dilation catheter relative to an opening of the Eustachian tube based on a distance of the marker from a proximal end of the balloon.

14. The method of claim 10, further comprising applying at least one substance to the Eustachian tube using the balloon dilation catheter.

15. The method of claim 14, wherein the substance is selected from the group consisting of contrast agents, antimicrobials, anesthetics, vasoconstrictors, analgesics, agent, a corticosteroids, anti-inflammatories, decongestants, mucous thinners, expectorants, mucolytics, surfactants, antihistamines, cytokine inhibitors, leucotriene inhibitors, IgE inhibitors, immunomodulators, allergens, hemostatic agents, antiproliferatives, cytotoxic agents, proteins, stem cells, genes and gene therapy preparations.

16. The method of claim 10, wherein advancing the balloon dilation catheter further comprises placing the user's index finger on the proximal flange of the actuator or in between the proximal and distal flanges of the actuator to advance the balloon dilation catheter.

17. A method for dilating a Eustachian tube of a patient having a nostril, the method comprising:
(a) inserting a balloon dilation catheter that includes an elongate shaft and a balloon attached to the elongate shaft into the nostril of the patient, the elongate shaft having a proximal end and a distal end, the balloon dilation catheter includes actuator coupled to the elongate shaft between the proximal and distal ends of the elongate shaft, wherein the actuator separates the elongate shaft into a flexible proximal portion and a distal portion, the distal portion having a rigid middle portion and a flexible distal portion, the actuator including a proximal flange extending orthogonally from an axis defined by the elongate shaft, a distal flange extending orthogonally from the axis of the elongate shaft, and a space disposed between the proximal and distal flanges that receives a user's thumb or index finger;
(b) advancing the balloon dilation catheter by moving the actuator using the user's thumb or index finger disposed in the space between the proximal and distal flanges, until the distal flange the actuator is adjacent to the nostril of the patient;
(c) expanding the balloon to dilate a portion of the Eustachian tube;
(d) collapsing the balloon; and
(e) removing the balloon dilation catheter from the nostril of the patient, wherein the dilated portion of the Eustachian tube remains at least partially dilated after removal of the balloon dilation catheter.

18. The method of claim 17, wherein the proximal flange extends parallel to the distal flange.

19. The method of claim 17, wherein the actuator is secured to the elongate shaft using an adhesive.

20. The method of claim 17, wherein the Eustachian tube includes an isthmus, wherein the balloon dilation catheter includes an atraumatic distal tip preventing the balloon dilation catheter from passing through the isthmus of the patient.

* * * * *